(12) United States Patent
Rekik

(10) Patent No.: US 9,155,719 B2
(45) Date of Patent: Oct. 13, 2015

(54) N-ACETYL-DL-LEUCINE, NEUROPROTECTIVE AND RETINOPROTECTIVE MEDICAMENT

(76) Inventor: Raouf Rekik, Montplaisir (TN)

(*) Notice: Subject to any disclaimer, the term of this patent is extended or adjusted under 35 U.S.C. 154(b) by 0 days.

(21) Appl. No.: 13/701,300

(22) PCT Filed: May 6, 2011

(86) PCT No.: PCT/IB2011/000965
§ 371 (c)(1),
(2), (4) Date: Feb. 8, 2013

(87) PCT Pub. No.: WO2011/151685
PCT Pub. Date: Dec. 8, 2011

(65) Prior Publication Data
US 2013/0142888 A1    Jun. 6, 2013

(30) Foreign Application Priority Data
Jun. 3, 2010  (TN) .................................. 2010/0251

(51) Int. Cl.
*A61K 31/198* (2006.01)
*A61K 45/06* (2006.01)

(52) U.S. Cl.
CPC .............. *A61K 31/198* (2013.01); *A61K 45/06* (2013.01)

(58) Field of Classification Search
CPC ...... A61K 31/198; A61K 45/06; A61K 38/00
See application file for complete search history.

(56) References Cited

U.S. PATENT DOCUMENTS

| 4,837,219 | A   |       | 6/1989  | Hutterer        |         |
|-----------|-----|-------|---------|-----------------|---------|
| 2008/0108702 | A1 | *   | 5/2008  | Przybylski      | 514/561 |
| 2009/0318555 | A1 |     | 12/2009 | Fabre et al.    |         |

FOREIGN PATENT DOCUMENTS

| EP | 1 582 207 A1 | 10/2005 |
| EP | 1 629 840 A1 | 3/2006 |
| EP | 2 098 124 A1 | 9/2009 |
| JP | 60 255722 A | 12/1985 |
| JP | 3 068514 A | 3/1991 |
| JP | 2003 221327 A | 8/2003 |
| JP | 2007 039367 A | 2/2007 |
| JP | 2008 024675 A | 2/2008 |
| WO | 2004/028536 A1 | 4/2004 |
| WO | WO 2004028536 A1 * | 4/2004 |
| WO | 2005/023368 A1 | 3/2005 |
| WO | 2010/065723 A1 | 6/2010 |
| WO | WO 2010065723 A1 * | 6/2010 |
| WO | 2010/137979 A2 | 12/2010 |

OTHER PUBLICATIONS

Lynch, C.J. J. Nutr. 2001, 861S-865S.*
Lynch, C.J. "Role of Leucine in the Regulation of mTOR by Amino Acids: Revelations from Structure—Activity Studies" Am Soc Nutr Sci 2001, pp. 861S-865S.*
International Search Report mailed Jul. 20, 2011, in connection with International Application No. PCT/IB2011/000965, filed May 6, 2011.
Shigemitsu, Kaori, et al., "Structural requirement of leucine for activation of p70 S6 kinase," FEBS Letters, 1999, vol. 447, pp. 303-306.

* cited by examiner

*Primary Examiner* — Sean Basquill
*Assistant Examiner* — Andrew S Rosenthal
(74) *Attorney, Agent, or Firm* — Duane Morris LLP; Gregory M. Lefkowitz

(57) ABSTRACT

The invention relates to a medicament, the active principle of which is a leucine and, for example, a N-ACETYL-DL-LEUCINE. It can be applied to the prevention and/or treatment of eye diseases or disorders and especially of hereditary dystrophies of the retina, glaucomatous neuropathy, glaucoma, macular degeneration, myopia, presbyopia, hypermetropia, astigmatism, all the ophtalmologic diseases or disorders inducing a decrease of visual function and/or age-related physiological vision decline.

13 Claims, No Drawings

N-ACETYL-DL-LEUCINE, NEUROPROTECTIVE AND RETINOPROTECTIVE MEDICAMENT

CROSS-REFERENCE TO RELATED APPLICATIONS

This application is a §371 national stage entry of International Application No. PCT/IB2011/000965, filed May 6, 2011, which claims priority to Tunisian patent Application No. TN2010/0251 filed Jun. 3, 2010, the entire contents of which are incorporated herein by reference.

FIELD AND BACKGROUND OF THE INVENTION

The invention relates to the production of medicaments, and especially of neuroprotective and retinoprotective medicaments (or drugs) for the prevention and/or the treatment of ophthalmologic conditions leading to damage to the retina and to the optic nerve, which result in a loss of vision (especially far and near visual acuity, contrast vision, color vision and/or visual field). These medicaments comprise at least one active principle which is a leucine, for example, the N-acetyl-DL-leucine. This leucine can be associated with other active principles and, in particular, with Ramipril or Ramiprilate.

The invention especially aims to provide medicaments intended for the prevention and/or the treatment of ophthalmologic diseases or disorders, which can improve visual function, in particular, far and/or near visual acuity, contrast vision, color vision and/or visual field, in patients suffering from chorioretinal and/or optic nerve diseases. Examples of such diseases or disorders that can be mentioned are:
- hereditary dystrophies of the retina, for example, pigmentosa retinopathy or stargardt's disease;
- glaucomatous neuropathy and more generally glaucoma;
- age-related macular degeneration (ARMD) and myopic macular degeneration.

The invention also aims to provide medicaments intended for the prevention and/or the treatment of visual refractive disorders, especially myopia, hypermetropia, presbyopia, astigmatism, and for stabilizing and improving vision in patients that have such visual refractive disorders.

The medicaments according to the invention are not limited to the above-mentioned uses. They can be used efficiently in preventing or slowing down, or even stopping, the age-related "natural" decreases in visual acuity or visual field or both at the same time.

Indeed, mean retinal sensitivity reduces linearly with age. This decline starts very early on, from 20 years of age, and accelerates after the age of 60.

In particular, the mean sensitivity (MS) expressed in decibels (dB) obeys the following equation, according to Jaffe: MS (dB)=28.8−0.074×age.

As shown in the examples, administration of N-acetyl-DL-leucine to patients via the systemic route (especially in an oral or injectable form) or the topical route (especially in the form of eye drops, an ointment or a cream) improved visual acuity, contrast vision, color vision but also visual field.

The N-acetyl-DL-leucine ($C_8H_{15}NO_3$) is a small molecule, with a relatively simple chemical structure. This optically inactive product is the result of N-acetylation of α-amino-isocaproic acid ($C_6H_{13}NO_2$), the L isomer of which, leucine, is a widespread natural α-amino acid.

Leucine:

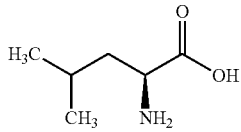

The N-acetyl-DL-leucine has the following formula:

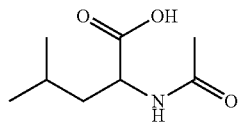

The effect of N-acetyl-DL-leucine on experimental vertigo in mice was discovered in 1957. Since this date, this compound is used successfully in human clinical medicine as a symptomatic medicament in vertigo states.

The N-acetyl-DL-leucine is widely prescribed by the doctors, well known from the pharmacists under the name Tanganil® (Pierre Fabre Medicament), and its efficiency is appreciated from many patients suffering from vertigo. However, the mechanism of action of this medicament is still subject to controversy.

The N-acetyl-DL-leucine was first disclosed by Emil Ficher, a very famous Professor of Chemistry at the University of Berlin, whose work in biochimistry and biological organic chemistry was rewarded by the Nobel Prize for Chemistry in 1902. The year before, in 1901, he published the preparation of the racemic acetyl derivative of leucine, obtained by reacting a solution of acetic anhydride in acetic acid with the amino acid ester.

Although the N-acetyl-DL-leucine has a favorable effect on vertigo, its potential for ophthalmologic applications was unknown before the present invention was made.

As disclosed herein, in the examples, observations based on real assays were made in patients having a glaucomatous neuropathy or a glaucoma, a hereditary dystrophy of the retina (for example, pigmentosa retinopathy or stargardt's disease), macular degeneration, myopia, hypermetropia, presbyopia or astigmatism, hemeralopia or a age-related physiologic loss of vision.

Hence, the invention relates to the use of a leucine and especially of the N-acetyl-DL-leucine, for the manufacture of medicaments intended for improving visual acuity and/or visual field in treated patients.

SUMMARY OF THE INVENTION

The invention relates to a leucine for use in a neuroprotective and/or retinoprotective ophthalmologic medicament. Said leucine can be, in particular, the N-acetyl-DL-leucine, one of its pharmaceutically acceptable salts or a derivative thereof.

This leucine can be used in the prevention and/or treatment of a loss of vision, which can be a "natural" loss of vision or a deterioration of vision resulting from an ophthalmologic condition.

The invention further relates to a composition comprising: a leucine, an angiotensin-converting enzyme inhibitor, a pharmaceutically acceptable vehicle and optionally, an additional active principle which is chosen among folic acid, magnesium, potassium, L-arginine, H4b, vitamin B6, vitamin B12, vitamin C, w-3 fatty acids, glucose, and mixtures thereof. This composition can be used as a neuroprotective and/or retinoprotective ophthalmologic medicament.

The invention is also directed to a method of preventing and/or treating one or several disease(s) or disorder(s) in an animal in need thereof, and to a method for maintaining or improving vision in an animal in need thereof. Said methods comprise administering to said animal a leucine as defined herein, the composition of the invention, or the active principles of the kit of the invention.

The invention also relates to a kit appropriate to carry out a method of the invention, and especially to a kit comprising a leucine or the composition of the invention and, optionally, instructions for using said kit.

A leucine or the composition or the kit of the invention can also be used in the prevention and/or the treatment of neurodegenerative diseases and, in particular, of Parkinson disease, Alzheimer disease, a multiple sclerosis or an amyotrophic lateral sclerosis.

DETAILED DESCRIPTION OF THE PREFERRED EMBODIMENTS OF THE PRESENT INVENTION

Unless otherwise indicated, each embodiment disclosed herein is applicable independently of and/or in combination with any one or several of the other described embodiments.

The term "vision" or "visual function" as used herein encompasses visual acuity (more especially near and/or far visual acuity) as well as contrast vision, color vision and field of vision (or visual field).

The term "loss of vision" or "degradation of visual function" as used herein includes partial or total loss of vision, and especially a partial or total loss in visual acuity (near and/or far visual acuity) and/or contrast vision and/or color vision and/or field of vision. It can result from a "natural" visual decline (i.e., it appears in the absence of any apparent eye disease or disorder), for example, in an aging animal, and/or from one or several ophthalmic condition(s) (in particular, an eye disorder and/or an eye disease) as disclosed herein.

The terms "treating" and "treatment" mean that an ophthalmologic condition (in particular, an eye disorder and/or an eye disease) is improved (at least partially) and, in particular, that the visual acuity and/or the contrast vision and/or the color vision and/or the field of vision of the treated animal is improved, or that the process of degradation of visual function is stopped.

As used herein, the term "ophthalmologic conditions" (or eye conditions) encompasses ophthalmologic disorders and ophthalmologic diseases involving chorio-retinal and/or optic nerve, resulting in a progressive loss of vision.

The term "ophthalmologic disorder" (or eye disorder) as used herein encompasses a change in vision, in the appearance of the eye or having abnormal sensations in the eye. It includes optic nerve disorders and chorio-retinal disorders, as well as trauma such as injuries to the eye, and especially disorders resulting in a progressive visual degradation or loss of vision.

As used herein, the term "ophthalmologic disease" (or eye disease) means any disease of the eye and, in particular, any disease of the eye resulting in a progressive loss of vision.

This terminology encompasses ophtalmologic diseases comprising a retina and/or optic nerve damage, and especially the following diseases of the eye:
diabetic retinopathy
hereditary dystrophies of the retina, in particular, pigmentosa retinopathy and stargardt's disease;
glaucomatous neuropathy and more generally glaucoma;
macular degeneration, in particular, age-related macular degeneration (ARMD) and myopic macular degeneration;
myopia, hypermetropia, astigmatism;
presbyopia;
age-related vision degradation;
night vision decline, and especially hemeralopia; and
a natural loss of vision and, in particular, physiologic visual decline, for example, age-related physiological vision decline.

The term "animal" as used herein includes mammalians, in particular, humans and non human mammalians, and birds.

The term "mammalian" or "mammal" as used herein encompasses any of various warm-blooded vertebrate animals of the class Mammalia, including humans and non human mammals, characterized by a covering of hair on the skin and, in the female, milk-producing mammary glands for nourishing the young.

By "topical administration" it is meant herein an administration which has a local effect. This term includes especially a sub-tenonian administration, or an administration to the eye (especially an intra- or extra-ocular administration).

The administration to the eye can be performed, for example, by applying active principle(s) as disclosed herein (which can be, for example, in the form of an ophtalmologic solution, an ointment or eye drops) to the outside surface of the eye, i.e., by contacting the eye and especially the cornea with said active principle(s).

Alternatively or cumulatively, the administration to the eye can be performed by injecting active principle(s) into the eye and especially into the vitreous (i.e., via intravitreal injection), for example, in the form of an ophtalmologic solution.

Active principles can be administered to the eye (for example, by application to the outside surface of the eye and/or by intraocular injection) using a delivery device which provides a controlled release of active principle(s) on the surface of the eye or into the eye. Said device can be, for example, placed in the lower cul de sac or conjunctival cul-de-sac, below the cornea, or injected into the eye, especially into the vitreous.

By "topical form", it is meant herein a form appropriate for topical administration, and especially a solution (in particular, an ophthalmologic solution), a lotion, drops (in particular, eye drops), a cream or an ointment.

As used herein, the term "pharmaceutically acceptable vehicle" encompasses an ophthalmologically acceptable vehicle (or carrier).

The term "ophthalmologically acceptable vehicle" as used herein means any vehicle that has substantially no long term or permanent detrimental effect on the eye to which it is administered, in particular, any vehicle that can be placed in the eye and that does not cause eye irritation. Opthamologically acceptable vehicles include water (distilled or deionized water), saline solutions, phosphate buffered saline solutions, physiological serum, and other aqueous media.

By "consisting essentially of", it is meant herein that minor ingredients can be added without having a major effect on active principles used in a composition, a medicament, a kit or a method as disclosed herein.

By "several", it is meant herein at least two (i.e., two or more than two) and, for example, three, four, five, six, seven, eight, nine, ten or more than ten.

The terms "magnesium" and "potassium" encompass respectively any form of magnesium and potassium, and especially a pharmaceutically acceptable salt of magnesium and potassium, for example, magnesium chloride and potassium chloride.

In a first aspect, the invention relates to a leucine or a pharmaceutically acceptable salt thereof or a derivative thereof, for use in a medicament, and especially for use in a neuroprotective and/or retinoprotective ophthalmologic medicament, in an animal (especially a human or non human mammal) in need thereof.

In one embodiment of the invention, the leucine is an acetyl-leucine, for example, an N-acetyl-leucine, one of its pharmaceutically acceptable salts or a derivative thereof.

The N-acetyl-leucine can be chosen from N-acetyl-DL-leucine, N-acetyl-L-leucine and N-acetyl-D-leucine, one of their pharmaceutically acceptable salts or a derivative thereof. More especially, the N-acetyl-leucine can be N-acetyl-DL-leucine, one of its pharmaceutically acceptable salts or a derivative thereof. For example, it can be Tanganil®.

In another embodiment of the invention, the leucine is a DL-leucine one of its pharmaceutically acceptable salts or a derivative thereof.

In an embodiment of the invention, the neuroprotective and/or retinoprotective ophthalmologic medicament is for use in preventing or slowing down, or even stopping loss of vision and especially for use in maintaining or improving visual acuity and/or contrast vision and/or color vision and/or visual field. This loss of vision can be a natural loss of vision, in particular, in an aging animal (especially an aging human or non human mammal). Alternatively or cumulatively, this loss of vision can be a deterioration of vision resulting from an ophthalmologic condition.

Hence, in an embodiment of the invention, a leucine is used in a medicament, a composition, a kit, or a method according to the invention as disclosed herein, for the prevention and/or the treatment of one or several ophthalmologic condition(s) which comprise(s) a deterioration (or loss) of vision and, in particular, one or several ophthalmologic condition(s) as disclosed herein, in an animal (especially a human or non human mammal) in need thereof.

In an embodiment of the invention, the ophtalmologic condition(s) prevented or treated according to the invention is (are) chosen from:
   diabetic retinopathy
   hereditary dystrophies of the retina, for example, pigmentosa retinopathy or stargardt's disease;
   glaucomatous neuropathy;
   glaucoma;
   macular degenerations, for example, ARMD or myopic macular degeneration.
   Cumulatively or alternatively, the ophtalmologic condition(s) can be chosen from visual refractive disorders, and especially from myopia, hypermetropia, presbyopia and astigmatism.

Cumulatively or alternatively, the ophtalmologic condition(s) can be a natural loss of vision and, in particular, age-related physiological vision decline and/or a night vision decline, especially hemeralopia.

In an embodiment of the invention, the medicament comprises a pharmaceutically acceptable vehicle enabling administration of said medicament in an oral, parenteral, intravenous, intramuscular, transdermal or topical form (especially in the form of eyedrops) in an animal in need thereof. As a way of illustration, the medicament according to the invention can be in the form of a tablet, a solution (especially an ophthalmologic solution), a lotion, drops (especially eye drops), a cream or an ointment.

In another embodiment of the invention, the medicament according to the invention is in a form appropriate for topical administration, in particular, topical administration to the eye, including a topical form appropriate for application to the outside surface of the eye, for intraocular or intravitreal injection, and/or for sub-tenonian administration, in an animal in need thereof. For example, the medicament can be in the form of eye drops. The medicament can be administered topically as disclosed herein.

In another aspect, the invention relates to the use of a leucine as defined herein, and especially of the N-acetyl-DL-leucine, in the prevention and/or the treatment of a neurodegenerative disease and, in particular, of a Parkinson disease, an Alzheimer disease, a multiple sclerosis or an amyotrophic lateral sclerosis.

In another aspect, the invention relates to pharmaceutical compositions in which the above-mentioned active principle is associated with one or several pharmaceutically acceptable vehicle(s), which allow their administration in different forms, and, in particular: oral, parenteral, intravenous, intramuscular and local or topical form, and especially in a topical form appropriate for administration to the eye. Forms appropriate for topical administration to the eye include the ones which are appropriate for application to the outside surface of the eye (especially eye drops or ophthalmologic solutions), for intraocular administration (or injection) and, in particular, for intravitreal injection (especially ophthalmologic solutions), and/or for sub-tenonian administration.

Hence, the invention relates to a composition, in particular, to a pharmaceutical composition (or drug or medicament), characterized in that it comprises, consists essentially of, or consists of:
   a) one or several leucine(s) as defined herein, for example, the N-acetyl-DL-leucine; and
   b) one or several pharmaceutically acceptable vehicle(s), for example, an ophthalmologically acceptable vehicle as defined herein; and
   c) optionally, one or several additional active principle(s) chosen among: an angiotensin-converting enzyme inhibitor (also called ACEI herein), folic acid, magnesium, potassium, L-arginine, H4b (or tetrahydrobiopterin), vitamin B6, vitamin B12, vitamin C, w-3 fatty acids and glucose.

In an embodiment of the invention, the composition comprises, consists essentially of, or consists of:
   a) one or several leucine(s) as defined herein, for example, the N-acetyl-DL-leucine;
   b) an ACEI; and c) a pharmaceutically acceptable vehicle, for example, an ophthalmologically acceptable vehicle as defined herein; and
d) optionally, an additional active principle which is chosen among: folic acid, magnesium, potassium, L-arginine, H4b, vitamin B6, vitamin B12, vitamin C, w-3 fatty acids, glucose, and mixtures thereof.

In an embodiment of the invention, the composition of the invention is a cell protective, neuroprotective and/or retinoprotective composition.

Hence, in one aspect, the invention relates to a neuroprotective and/or retinoprotective ophthalmologic composition or medicament, which is suitable for preventing, slowing down or interrupting (or stopping) the process of vision loss or even reversing its course in an animal (especially a human or non human mammal) and, in particular, in an aging animal and/or in an animal with one or several eye ophthalmologic condition(s). This composition or medicament is characterized in that its active ingredient or one of its active ingredients is a leucine defined herein, for example, the N-acetyl-DL-leucine.

In an embodiment of the invention, the composition or medicament is suitable for and/or used for maintaining or improving vision in an animal, and, in particular, in an aging animal and/or in an animal with an eye disease or disorder.

Alternatively or cumulatively, said composition or medicament can also be suitable for and/or applied to a normal subject, i.e., to an animal which does not have any apparent eye disease or disorder, for maintaining eye vision (i.e., for preventing a loss of vision) or even for improving vision.

In an embodiment of the invention, the ACEI is more lipophilic in nature than Enalaprilat. In particular, the ACEI can comprise, consist essentially of, or consist of Ramipril, Ramiprilat (which results from de-esterification of Ramipril), one of their pharmaceutically acceptable salts, or any other derivative of Ramipril or Ramiprilat that can liberate Ramipril or Ramiprilat into the animal to which the active principle is administered, or a mixture thereof. For example, the ACEI can comprise, consist essentially of, or consist of Ramipril, which is marketed, in particular, as Tritace®, Altace®, Triatec® or Delix®, has the following formula:

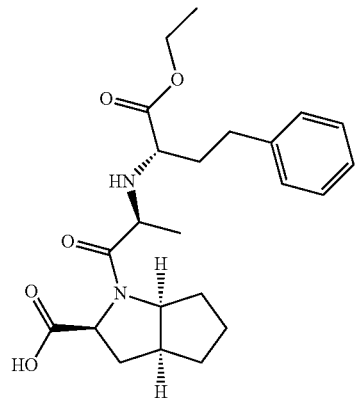 [SMILES: CCOC(=O)[C@H](CCc1ccccc1)N[C@@H](C)C(=O)N1[C@H](C(=O)O)C[C@@H]2CCC[C@@H]21]

In an embodiment of the invention, the additional active principle is folic acid, magnesium, potassium, L-arginine, H4b, vitamin B6, vitamin B12, vitamin C, w-3 fatty acids or glucose.

In an embodiment of the invention, the composition, the medicament or the kit of the invention comprises, consists essentially of, or consists of a leucine (as disclosed herein) and the active principle(s) as set forth in Table 1.

Any w-3 fatty acids can be used according to the invention, and, in particular, a α-linolenic acid (ALA), a eicosapentaenoic acid (EPA), or a docosahexaenoic acid (DHA).

TABLE 1

| Examples of active principle(s) that can be combined with leucine | | | | | | | | | | | | | | | | | | | | | | |
|---|---|---|---|---|---|---|---|---|---|---|---|---|---|---|---|---|---|---|---|---|---|---|
| ACEI and/or Folic acid | x | | x | x | | x | x | | | x | x | | x | x | | | x | x | | x | x | | x |
| Mg and/or K | | x | | x | | x | x | | x | | x | x | x | | x | | x | | x | x | | x | x |
| Glucose | | | x | | x | x | x | | | x | | x | x | x | | x | | | x | x | x | | x |
| L-arginine | | | | | | | | x | x | x | x | x | x | x | | | | | | | x | x | x |
| B6 and/or B12 and/or C | | | | | | | | | | | | | | | x | x | x | x | x | x | x | x | x |
| H4b and/or w-3 fatty acid(s) | | | | | | | | | | | | | | | | | | | | | | | |

| Examples of active principle(s) that can be combined with leucine | | | | | | | | | | | | | | | | | | | | | | |
|---|---|---|---|---|---|---|---|---|---|---|---|---|---|---|---|---|---|---|---|---|---|---|
| ACEI and/or Folic acid | x | | x | x | | | x | x | | x | x | | x | x | | x | x | | | x | x | | x x |
| Mg and/or K | | x | x | | x | | x | | x | x | | x | | x | x | | x | | x | | x | x | x |
| Glucose | x | x | x | | | x | | x | x | x | | x | | x | x | x | | x | | x | x | x | x |
| L-arginine | x | x | x | x | x | x | x | x | x | X | | | x | | | x | x | x | x | x | x | x | x |
| B6 and/or B12 and/or C | x | x | x | | | | | | | | x | x | x | x | x | x | x | x | x | x | x | x | x |
| H4b and/or w-3 fatty acid(s) | | | | x | x | x | x | x | x | x | x | x | x | x | x | x | x | x | x | x | x | x | x |

Examples of active principles that can be associated with a leucine in the composition, the medicament, the methods and the kit of the invention. The presence of an active principle is indicated by an "x".
By "ACEI and/or Folic acid", it is meant ACEI (for example Ramipril) or folic acid or ACEI (for example Ramipril) and folic acid.
By "Mg and/or K", it is meant magnesium, or potassium or both magnesium and potassium.
By "B6 and/or B12 and/or C", it is meant vitamin B6 or vitamin B12 or vitamin C or vitamin B6 and vitamin B12 or vitamin B6 and vitamin C or vitamin B12 and vitamin C or vitamin B6 and vitamin B12 and vitamin C.
By "H4b and/or w-3 fatty acid(s)", it is meant H4b or w-3 fatty acid(s) or H4b and w-3 fatty acid(s).
The ACEI, the magnesium and the potassium are as disclosed herein.

In an embodiment of the invention, the pharmaceutically acceptable vehicle is appropriate for enteral (for example, oral), parenteral (for example, intravenous, intramuscular or subcutaneous), transdermal, or topical administration (for example, topical administration to the eye, and especially application to the outside surface of the eye, intraocular or intravitreal injection and/or sub-tenonian administration) in an animal in need thereof.

In an embodiment of the invention, the composition or the medicament according to the invention is in the form of a tablet, a solution, a lotion, drops, a cream or an ointment.

In another embodiment of the invention, the composition or the medicament according to the invention is in the form of an ophthalmic solution or eye drops, such a composition being obtainable, for example, by diluting the active principles in an opthamologically acceptable vehicle, for example, in a physiological serum.

In another aspect, the invention relates to a composition as disclosed herein, for use as a medicament. In particular, this composition can be used as a cellprotective, a neuroprotective and/or a retinoprotective medicament, and especially as a neuroprotective and/or a retinoprotective medicament.

In one embodiment of the invention, the composition, the medicament, the kit or a method according to the invention is appropriate for and/or used for the prevention or the treatment of any one or several disease(s) or disorder(s) chosen from: ophthalmologic conditions (as disclosed herein), neurodegenerative conditions (for example, Alzheimer disease, Parkinson disease, an amyotrophic lateral sclerosis and/or a multiple sclerosis), cancers (for example, carcinoma, and more especially adeno-carcinoma), arterial hypertension, hyperlipemia, coronary heart disease, atherosclerosis, diabetes, rheumatism, general inflammatory and immune conditions and infections (for example, viral and especially HIV infection, bacterial infection and/or parasitic infection).

In another embodiment of the invention, the composition, the medicament, a kit, or a method according to the invention is for use in the prevention or the treatment of ophthalmologic conditions (especially ophthalmologic disease(s) or disorder(s) as disclosed herein) and/or neurodegenerative conditions (for example, Alzheimer disease, Parkinson disease, an amyotrophic lateral sclerosis and/or a multiple sclerosis).

In an embodiment of the invention, a composition, a medicament, a kit or a method according to the invention is used to prevent, slow down, stop or even reverse (at least partially) a loss of vision, said loss of vision resulting, for example, from a natural visual decline and/or from one or several ophthalmologic disorder(s) or disease as disclosed(s) herein.

Hence, in an embodiment of the invention, a composition, a medicament, a kit or a method according to the invention is intended for use and/or is used for maintaining or improving (i.e., increasing) eye vision, for example, in a normal animal and/or in an aging animal (especially an aging human or non human mammal) and/or in an animal having one or several ophthalmologic condition(s) as disclosed herein.

The composition, the medicament, the kit or a method according to the invention can in particular be used for maintaining or improving vision of one or both eyes, especially in a normal animal and/or in an aging animal (especially an aging human or non human mammal) and/or in an animal having a ophthalmologic condition as disclosed herein.

In another aspect, the invention relates to the use of a leucine as disclosed herein, and optionally of other active principles as disclosed herein, for the manufacture (or preparation) of a composition, a medicament or a kit (as disclosed hereinafter), which composition, medicament or kit can be intended for a use as disclosed herein.

The invention also relates to a composition or a kit as disclosed herein, for the manufacture of medicament and, in particular, a neuroprotective and/or a retinoprotective medicament, said medicament being intended for a use as disclosed herein.

The composition, the medicament and the kit according to the invention are appropriate for caring out a method as disclosed herein.

In a further aspect, the invention relates to a kit which comprises or consists of:—a leucine as defined herein, or a composition of the invention; and optionally, instructions for using said kit (for example, in a method of the invention).

In an embodiment of the invention, the kit comprises or consists of:

(i) a leucine as disclosed herein; and one or several compounds chosen from (ii) an ACEI as disclosed herein and/or (iii) an additional active principle chosen among: folic acid, magnesium, potassium, L-arginine, H4b, vitamin B6, vitamin B12, vitamin C, w-3 fatty acids, glucose, and mixtures thereof; and optionally, (iv) instructions for using said kit (for example, in a method of the invention).

Examples of active principles that can be associated with a leucine in a kit of the invention are disclosed in table 1.

The active principles (i) and (ii) and/or (iii) can be present in the same composition (i.e., a composition of the invention). Alternatively, at least two of these active principles can be present in separate compositions.

The term "present in the same composition" (or "associated in the same composition") means that a) the leucine and b) the ACEI and/or the additional active principle are in the form of one single composition, i.e., that the kit comprises a composition of the invention.

Alternatively, when "at least two of these active principles are in separate compositions", this means that the kit of the invention comprises at least two or three separate compositions, each of these compositions comprising, consisting essentially of, or consisting of at least one or two of these active principles (and a pharmaceutically acceptable vehicle, especially an ophthalmologically acceptable vehicle):

said kit may comprise only two separate compositions
when one of the active principle (ii) or (iii) is not present in the kit (in this case, one composition comprises the leucine and the other composition comprises the active principle (ii) or (iii) which is present); or
when the active principles (ii) and (iii) are both present in the kit but either (i), (ii) or the (iii) is separated from the two other active principles in a separate composition, the two other active principles being present in the same composition; and said kit may comprise at least three separate compositions
when both (ii) and (iii) are present in the kit and when each of the three active principles (i), (ii) and (iii) is present in a separate composition (i.e., each of these three compositions comprises, consists essentially of, or consists of one of the three active principles (i), (ii) or (iii), and a pharmaceutically acceptable vehicle, especially an ophthalmologically acceptable vehicle).

Or course, when active principle (i) or active principle (ii) which is used in the kit or the methods of the invention comprises a mixture of several active principles, these active principles can be present in the same composition or alternatively at least two of these active principles can be in separate compositions.

The at least two or three separate compositions that can be present in the kit of the invention can be administered either simultaneously or not (in any order) to an animal (especially a human or non human mammal), for example, to carry out a method of the invention.

In an embodiment of the invention, the composition(s) comprising the active principle (i) and/or the active principle (ii) and/or the active principle (iii) is(are) neuroprotector and/or retinoprotector composition(s).

In an embodiment of the invention, the active principles (i), (ii) and (iii) (if present in the kit of the invention) are associated with pharmaceutically acceptable vehicle(s) allowing their administration in the administration forms disclosed herein.

In an embodiment of the invention, at least two of the active principles (i), (ii) and (iii) of the kit are in separate compositions, and at least one of these separate compositions is formulated in a topical form (especially a topical form appropriate for administration to the eye and, in particular, a form appropriate for application to the outside surface of the eye, for intraocular or intravitreal injection and/or sub-tenonian administration), for example, in the form of an ophthalmic solution or eye drops. In this case, the other separate composition(s) can be formulated either in a topical form (especially a topical form appropriate for administration to the eye and/or sub-tenonian administration) or in another administration form, for example, in an oral form.

When the composition, a medicament or a kit according to the invention are intended for treating other type(s) of diseases, and especially a neurodegenerative disease, any form of administration can be used, for example, any form appropriate for oral or parenteral administration.

In a further aspect, the invention relates to a method of preventing and/or treating one or several disease(s) or disorder(s) (in particular, one or several eye condition(s) as disclosed herein) in an animal (especially a human or non human mammal) in need thereof, said method comprising (or consisting in) administering to said animal a leucine as defined herein or a composition of the invention, or the active principles of a kit of the invention. The active principles can be administered separately (i.e., in separate compositions) or not separately (for example, in a composition of the invention). The disease(s) or disorder(s) can be as defined herein.

In another aspect, the invention relates to a method for maintaining or improving vision in an animal (especially a human or non human mammal) in need thereof, said method comprising (or consisting in) administering to said animal a leucine as defined herein, or a composition of the invention, or the active principles of a kit of the invention, said active principles being administered separately (i.e., in separate compositions) or not separately.

By "administered separately or not", it is meant herein that the active principles are administered or not in the form of separate compositions. Hence, when the active principles are administered "separately", this means that at least two or three separate compositions are used: at least two separate compositions when no active principle (ii) or (iii) is used, and at least three separate compositions when at least the three active principles (i), (ii) and (iii) are used. By "not administered separately", it is meant herein that at least two of these active principles are administered in separate compositions (as disclosed herein for the kit of the invention). These separate compositions can be administered simultaneously or not (in any order) to the animal.

The methods of the invention can be performed using the kit of the invention.

Cumulatively or alternatively, the methods of the invention can comprise or consist in administering to an animal in need thereof a composition of the invention.

The active principle(s) can be administered according to a method of the invention by any one or several of the administration route(s) disclosed herein and especially by topical administration, for example, topical administration to the eye, including application to the outside surface of the eye, intraocular administration (or injection) and, in particular, intravitreal injection, and/or sub-tenonian administration.

In an embodiment of the invention, by "administering" it is meant herein applying active principles (for example, the leucine, and optionally the active principles (ii) and/or (iii) as disclosed herein) and, in particular, the composition of the invention to the outside surface of one eye or both eyes of an animal (especially a human or non human mammal), and, in particular, contacting the surface of one eye or of both eyes of an animal with said active principles or with a composition of the invention. The administered active principles or composition can be, for example, in the form of an ophtalmologic solution, eyedrops or an ointment.

Alternatively or cumulatively, in an embodiment of the invention, by "administering" it is meant herein injecting in one eye or both eyes, especially injecting into the vitreous of one eye or of both eyes of an animal (especially a human or non human mammal), active principle(s) (in particular, the leucine, and optionally the active principles (ii) and/or (iii) as disclosed herein), which active principle(s) can be, for example, in the form of an ophtalmologic solution.

The leucine and the active principle(s) (ii) and/or (iii) (or composition(s) comprising them) can be administered by the same route (for example, the topical route as disclosed herein) or via different routes, which routes can be chosen independently, for example, from the administration routes disclosed herein. In one embodiment of the invention, at least one of these active principles is administered by topical administration, in particular, by topical administration to the eye, including application to the outside surface of the eye, intraocular administration (or injection) and, in particular, intravitreal injection, and/or sub-tenonian administration, for example, in the form of an ophthalmic solution or eye drops.

In one aspect of the invention, the animal treated according to a method of the invention (especially according to the method for maintaining or improving vision according to the invention) has one or several ophthalmologic condition(s) as defined herein and/or is aged.

In an embodiment of the invention, a leucine, the composition, the medicament, the kit and/or the methods according to the invention are intended for or applied to a human being (or patient). In this embodiment, by "aged" or "aging" it is meant, for example, above the age of 50, above the age of 60 or above the age of 70.

When the ophthalmologic condition or one of the ophthalmologic conditions prevented or treated using a leucine, a medicament, a composition, a kit or a method according to the invention are a hereditary dystrophies of the retina (for example, pigmentosa retinopathy or stargardt's disease), the treated animal and especially the treated human being can, for example, be under the age of forty, preferably under the age of thirty, and more preferably under the age of twenty, for example, from 6 to 30, or from 6 to 20 years of age.

According to the invention, effective amounts and/or pharmaceutically acceptable amounts (especially physiologically or ophtalmologically acceptable amounts) of active principle(s) are used.

As a way of illustration, an active principle is usually administered to a human or an animal in order to prevent or treat an eye condition in a concentration ranging from 0.001 to 15% (w/v), preferably from 0.05 to 10% (w/v), and more preferably from 0.1 to 3% (w/v). In particular, an active principle in the form of eye drops can be used, for example, in a concentration ranging from 0.1 to 5% and more preferably from 0.5 to 3%, for example, in a concentration of 0.5%, 1% or 2%.

As a way of illustration, the following amounts of active principle can be administered to a human (in particular, for the prevention and/or the treatment of a loss of vision):
  leucine (especially the N-acetyl-DL-leucine):
    topical administration (for example, eye drops): 0.5 to 5% or 0.5 to 3%, for example, 0.5, 1 or 2%;
    oral administration: 0.5 to 5 g/day, preferably 1 to 3 g/day, for example, 2 g/day.
  Ramipril or Ramiprilate:
    topical administration (for example, eye drops): 0.5 to 5% or 0.5 to 3%, for example, 0.5, 1 or 2%;
    oral administration: 0.5 to 5 mg/day, preferably 1 to 2 mg/day, for example, 1.25 mg/day.
  folic acid:
    topical administration (for example, eye drops): 0.5 to 5% or 0.5 to 3%, for example, 0.5, 1 or 2%;
    oral administration: 2 to 8 mg/day, preferably 4 to 6 mg/day, for example, 5 mg/day.

The compositions or medicaments that contain the active principle(s) as defined herein may be administered to a mammalian eye (especially to a human eye) as often as necessary to obtain an improvement of the disorder(s) and/or disease(s) (and especially of the ophthalmic condition(s). Those skilled in the art will recognize that the frequency of administration and duration of treatment depends on the precise nature of the active principles and its concentration in the composition, and various factors such as the type and severity of the disorder or disease, the age and weight of the animal, the animal's general physical condition and the cause of the disorder or disease. Within these guidelines, it is contemplated that the ophthalmic composition (preferably, ophthalmic solutions or eye drops) of the present invention will be administered topically to the mammalian eye approximately once, twice or three times daily.

The duration of treatment administered in accordance with the present invention may range, for example, from a few weeks (at least one week) to a few months (at least one month), in particular, from 1 week to 6 months, preferably at least 2 weeks and less than 4 months and more preferably at least 3 weeks and less than 3 months. However, a prolonged treatment may be required. In particular, the treatment may last for one or several years or even for life, for example, in case of recurrence of the disorder(s) or disease(s) and especially of an ophthalmic condition.

Of course, one of several additional active principle(s), and especially one of several additional compounds for treating eye disorders and/or diseases may be used in the methods of the invention or may be present in a composition, a medicament or a kit according to the invention, provided that they do not interact with the active principles disclosed herein, to provide adverse side effects.

The invention will be illustrated further by the description of clinical examples which, of course, are not limiting in nature.

Examples

While the numerical indications given below should not be considered to be limiting in nature, since they can be left to the clinician and his or her patient, the following daily doses of active ingredient (for example, the N-acetyl-DL-leucine) are effective, in an amount of 2 gr per day, when administered orally, or in a concentration of 2% when administered in the form of eye drops. It is clear that the dosage may vary from one patient to another and that it is ultimately a matter for the clinician.

There is a clear preference for topical administration forms, in particular, in the form of eye eye drops. They have proven to be particularly effective.

In other words, the active ingredient (for example, the N-acetyl-DL-leucine) is combined with one or several pharmaceutical vehicles that enable clinical use thereof in the form of eye drops.

The invention will be even further illustrated by the description of the clinical examples which follow and which, of course, are not limiting in nature. In these examples, the active ingredient, the N-acetyl-DL-leucine, was administered continuously (i.e., at least once a day) in oral or topical form, in an amount of 2 gr per day in the case of the oral form and 2% in the case of eye drops.

It is notable that equivalent observations were made in "normal" patients, which do not present any ocular pathology (in particular, aging individuals), to whom the medicament was administered; these patients noticed an improvement of their vision, in particular, aging individuals regained the mean sensitivity that they experienced when they were much younger.

Clinical Observations

I) Hereditary Dystrophy of the Retina and Pigmentary Epithelium:
1—Retinitis Pigmentosa:
This disorder corresponds to a dystrophy in the photoreceptors (cones and rods). It is characterized by the appearance of night blindness in infancy or adolescence, progressive contractions of the equatorial annular peripheral visual filed and results in a substantial loss in visual acuity or even blindness by adulthood.
Evolution and Prognosis:
Prognosis is severe. It is characterized by a constant progression of the disorder towards blindness.
The N-acetyl-DL-leucine was used and induced an improvement of visual function: Seven patients were treated: three of them received 1 gr 2 times per day via oral administration; and four of them were subjected to a topical administration (2% eye drops), 3 times per day. All of them noticed an improvement of their visual acuity and visual field.
2—Starpardt's Disease:
Two twin patients treated with N-acetyl-DL-leucine in the form of eye drops noticed an improvement of their visual acuity by $1/10$ for one of them, and by $2/10$ to $3/10$ for the brother.
II) Age-Related or Myopia-Related Macular Degeneration:
Eleven patients with a macular degeneration which were treated with N-acetyl-DL-leucine (eye drops or tablets) noticed an improvement of their visual acuity.
III) Glaucomatous Neuropathy or Glaucoma:
Patients with known glaucoma experienced a decrease in their occular tension, and an improvement of their visual acuity and visual field in a very short time as soon as the treatment was administrated. Among the achieved effects are:
  visual acuity: marked improvement under N-acetyl-DL-leucine treatment, either by the oral route or the topical route (eye drops);
  visual field: regression of the deficiency after receiving N-acetyl-DL-leucine (via the oral route or in the form of eye drops).

IV) Ametropia.

This invention relates to the manufacture of a retinoprotective medicament, namely N-acetyl-DL-leucine via the general (systemic) route or the topical route (eye drops) for improving vision.

More particularly, but not exclusively, it relates to eyedrops composed of N-acetyl-DL-leucine, which are intended for improving (i.e., in the present case, decreasing) the effects of presbyopia, myopia, hypermetropia and astigmatism, for stabilizing them or even for reversing the evolutive course thereof.

Myopia: seven patients were evaluated and received the N-acetyl-DL-leucine in the form of eye drops.
  Result: in addition to the improvement of their visual acuity, the visual field, the refractive value was reduced. One can deduce therefrom that the N-acetyl-DL-leucine not only improves vision but also treats myopia.

Presbyopia: fourteen patients received the N-acetyl-DL-leucine in the form of eye drops and experienced an improvement of their near vision and a decrease in presbyopia. Some of them did not need any longer to wear a correction of the near vision. The N-acetyl-DL-leucine has proven to be an effective treatment of presbyopia.

Hypermetropia: the same observations as for presbyopia were made for hypermetropia.

Astigmatism: the astigmatic subjects noticed an improvement of their visual acuity under N-acetyl-DL-leucine treatment in the form of eye drops.

V) Night Vision:

Night vision of all the patients with visual difficulties at night (hemeralopia) was greatly improved under N-acetyl-DL-leucine treatment.

VI) Agr-Related Physiological Vision Decline:

In many cases, N-acetyl-DL-leucine improved visual function (visual acuity, contrast vision and visual field) in the absence of any occular pathology.

Although this is only a hypothesis that must be further explored, it appears that the mechanism(s) of action of N-acetyl-DL-leucine may be in relation with some of its chemico-physical aspects:

The N-acetyl-DL-leucine easily binds to various metal ions, especially to copper.
  The carbon gamma of this molecular agent, which is the tertiary carbon of the isobutylic part of the carbon chain, is sensitive to an attack by X-rays Gama-rays or by the hydroxyl moiety; the acetyl moiety enables leucine to cross the meningeal barrier and the neural barrier.

These two properties are significant of a strong antioxidant action of the N-acetyl-DL-leucine. It is known that any antioxidant action is correlated with an increased production of nitrogen monoxide (NO). Hence, the N-acetyl-DL-leucine may not only be an antioxidant product but also a product increasing NO production, which would thus explain two fundamental roles:

A PREVENTIVE AND CURATIVE ROLE in some chronic diseases (inherited retinal dystrophies; glaucoma neuropathy; macular degeneration; ametropia; etc).
  A ROLE IN PHYSIOLOGY and, in particular:
    1—ENERGY: NO increases mitochondrial calcium. Mitochondrial calcium is involved in the control of mitochondrial metabolism. Indeed, these calcium ions activate several enzymes of the citric acid cycle and control ATP production. The increase in calcium ions concentration is associated with an increase in the synthesis of mitochondrial ATP.
    The N-acetyl-DL-leucine may increase the energy which is available in the form of ATP.

2—VISION MECHANISM: visual transduction pathway:
    2/a In the dark, a constant current, which is named "dark current", is passing through the photo-receptive cells, which current results from the sodium ion flux which enters into the cytoplasm of the external segment via transmembrane cation channels which are cyclic guanosine 5' monophosphate (cyclic GMP, cGMP)-dependent.
    2/b: In the light, photon absorption by the photo-pigment leads to isomerisation of the chromophore which is changing from the 11-cis form to the totally-trans form and provides the opsine with the ability to activate transducine (T). T then stimulates an enzymatic effector, which is the phosphodiesterase (PDE). Activated PDE favors hydrolysis of cytosolic cGMP into 5'GMP. The decrease in the cGMP concentration causes closing of the cationic channels that are dependend from this nucleoside (CNCG). This closing interrupts the entering flux of sodium ions, changes positively et as a consequence causes a hyperpolarization wave in the plasma mambrane of the external segment. This wave is progressively passed on and reaches the synaptic ending where it is transmitted to the neuronal cells of the next layers.

All of these events last 100 millisecondes and activation of a rhodopsine molecule induces closing of 1000 cationic channels.

Desactivation of the Visual Transduction Pathway, or "Return to Dark":

Desactivation of the visual transduction pathway is a sine qua non condition for proper retinal functioning. Any hindrance to this desactivation, in other words, any prolonged or constant floodlighting of the retina, no matter if it is due to a prolonged light exposure or to mutations in a gene involved in the return to dark state, will lead to pathologic phenomenons. The return to dark implies a massive influx of sodium ions in the external segment of the photoreceptors and depolarization of the plasma membrane. Only a re-opening of the cationic channels, which re-opening is dependent on a significant increase in the cGMP cytosolic level, will allow reaching this goal.

cGMP production requires a good bio availibility in nitrogen monoxide (NO). The N-acetyl-DL-leucine, by reducing the free radicals and thus by increasing NO production, is involved in desactivation of the visual transduction pathway or "return to dark", which is a sine qua non condition for a proper vision physiology and thus which guarantees a good vision and a protection against the deleterious effects of a prolonged light exposure, a factor of chronical chorio-retinal and optic nerve pathologies.

From a molecular point of view, by opening the cationic channels by means of NO and then GMPc, N-acetyl-DL-leucine may lead to sodium and calcium influx and decrease photoreceptor hyperpolarization and bring them back towards their normal rest potential ("dark state").

The first experiments that aimed to understand the effect of this molecule on vertigo have shown that it acts directly on central vestibular neurons that are placed in abnormal depolarization or hyperpolarization conditions.

The important action of N-acetyl-DL-leucine on the neurons placed in an extreme hyperpolarization condition was confirmed by intracellular recordings.

Influx of sodium and calcium in the cell, which leads to the decrease of hyperpolarization and to a return of the neuroreceptor to a normal rest potential, allows for calcium cellular bioavailability, which ion is important in energy (ATP) production and for proper neuroreceptor functioning.eb;normal

What is claimed is:

1. A method for treating one or several ophthalmologic diseases, which are diseases comprising a retina and/or optic nerve damage and are selected from the group of hereditary dystrophies of the retina, comprising: pigmentosa retinopathy and stargardt's disease, in an animal in need thereof consisting of administering to said animal a medicament consisting essentially of a N-acetyl-DL-leucine or one of its pharmaceutically acceptable salts and an opthamologically pharmaceutically acceptable vehicle selected from the group consisting of distilled water, deionized water, saline solution, phosphate buffered saline solution, and physiological serum.

2. The method according to claim 1, wherein said pharmaceutically acceptable vehicle in said medicament can be administered in an oral or topical form.

3. The method according to claim 1, wherein said medicament is in a form for topical administration.

4. The method according to claim 1, wherein said medicament is in the form of eye drops.

5. The method according to claim 1, wherein said one or several of the neuroprotective and/or retinoprotective ophthalmologic diseases are glaucomatous neuropathy and/or glaucoma.

6. The method according to claim 1, wherein said one or several of the neuroprotective and/or retinoprotective ophthalmologic diseases are age-related macular degeneration and/or myopic macular degeneration.

7. The method according to claim 1, wherein said one or several of the neuroprotective and/or retinoprotective ophthalmologic diseases are myopia.

8. The method according to claim 1, wherein said one or several of the neuroprotective and/or retinoprotective ophthalmologic diseases are presbyopia.

9. The method according to claim 1, wherein said one or several of the neuroprotective and/or retinoprotective ophthalmologic diseases are refractive defects selected from the group of astigmatism and hypermetropia.

10. The method according to claim 1, wherein said one or several of the neuroprotective and/or retinoprotective ophthalmologic diseases are hemeralopia.

11. The method according to claim 1, wherein said one or several of the neuroprotective and/or retinoprotective ophthalmologic diseases are diabetic retinopathy.

12. The method according to claim 1, wherein said medicament is administered to a human in need thereof topically to the eye, in a concentration of 0.5 to 5%, and/or orally, in an amount of 0.5 to 5 g/day or 1 to 3 g/day.

13. A method for maintaining or improving vision in an animal suffering from a disease comprising a retina and/or optic nerve damage and selected from the group of hereditary dystrophies of the retina, comprising: pigmentosa retinopathy and stargardt's disease, said method consisting of administering to said animal a medicament consisting essentially of a N-acetyl-DL-leucine or one of its pharmaceutically acceptable salts and an opthamologically pharmaceutically acceptable vehicle selected from the group consisting of distilled water, deionized water, saline solution, phosphate buffered saline solution, and physiological serum.

* * * * *